US012788288B2

(12) United States Patent
Kossakovski et al.

(10) Patent No.: US 12,788,288 B2
(45) Date of Patent: Nov. 10, 2026

(54) ANALYTE TRANSPORTING MEMBRANES FOR USE WITH ANALYTE SENSORS

(71) Applicant: Medtronic MiniMed, Inc., Northridge, CA (US)

(72) Inventors: Dmitri A. Kossakovski, La Crescenta, CA (US); Ashwin K. Rao, West Hills, CA (US); Suryakiran Vadrevu, Santa Clarita, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 254 days.

(21) Appl. No.: 18/602,816

(22) Filed: Mar. 12, 2024

(65) Prior Publication Data

US 2024/0335147 A1 Oct. 10, 2024

Related U.S. Application Data

(60) Provisional application No. 63/494,428, filed on Apr. 5, 2023.

(51) Int. Cl.
*A61B 5/1486* (2006.01)
*A61B 5/145* (2006.01)

(52) U.S. Cl.
CPC ...... *A61B 5/14865* (2013.01); *A61B 5/14532* (2013.01)

(58) Field of Classification Search
CPC ........................ A61B 5/14865; A61B 5/14532
See application file for complete search history.

(56) References Cited

U.S. PATENT DOCUMENTS

| | | | |
|---|---|---|---|
| 4,755,173 | A | 7/1988 | Konopka et al. |
| 5,391,250 | A | 2/1995 | Cheney, II et al. |
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |

(Continued)

FOREIGN PATENT DOCUMENTS

| | | | |
|---|---|---|---|
| GB | 2609533 | A | 2/2023 |
| WO | 9941375 | A2 | 8/1999 |

OTHER PUBLICATIONS

Hansen et al., "Glucose Transport Machinery Reconstituted in Cell Models". Chem Commun (Camb). Feb. 11, 2015; 51(12): 2316-2319.

(Continued)

*Primary Examiner* — Eric F Winakur

(57) ABSTRACT

Embodiments of the invention provide amperometric analyte sensors having membranes made from materials selected to transport analytes such as glucose to an enzyme within the sensor while simultaneously inhibiting the movement of interfering species such as acetaminophen to the electrode within the sensor. While embodiments of the invention can be used in a variety of contexts, typical embodiments of the invention include glucose or ketone sensors used in the management of diabetes.

15 Claims, 8 Drawing Sheets

(56) References Cited

U.S. PATENT DOCUMENTS

| | | | |
|---|---|---|---|
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,751,130 | B2 | 7/2010 | Roux et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 11,045,119 | B2 | 6/2021 | Yoon et al. |
| 2007/0123819 | A1 | 5/2007 | Mernoe et al. |
| 2010/0160861 | A1 | 6/2010 | Causey, III et al. |
| 2022/0153778 | A1 | 5/2022 | Manzer et al. |

OTHER PUBLICATIONS

Kim et al., "A bio-inspired highly selective enzymatic glucose sensor using a red blood cell membrane". Analyst, 2020, 145, 2125-2132.

Thorens et al., "Glucose transporters in the 21st Century". Am J Physiol Endocrinol Metab 298: E141-E145, 2010.

Extended European Search Report dated Jul. 4, 2024 for EP Application No. 24166813.6.

Mark et al., "The effect of lipid bilayer manipulation on the response of the glucose oxidase-liposome electrode", Biosensors and Bioelectronics, vol. L2, No. 5, 1- , Jan. 1, 1997 (1997-0L-01) , pp. 467-477.

European Communication pursuant to Article 94(3) EPC dated May 30, 2025 for European Application No. 24166813.6.

European Communication pursuant to Article 94(3) EPC dated May 4, 2026 for European application No. 4166813.6.

Kim Young-Rok et al: "Synthetic Biomimetic Membranes and Their Sensor Applications", Sensors, vol. 12, No. 7, Jul. 11, 2012 (Jul. 11, 2012), pp. 9530-9550.

ANALYTE TRANSPORTING MEMBRANES FOR USE WITH ANALYTE SENSORS

CROSS REFERENCE TO RELATED APPLICATIONS

This application claims the benefit under 35 U.S.C. Section 119 (e) of commonly-assigned U.S. Provisional Patent Application No. 63/494,428, filed Apr. 5, 2023, entitled "ANALYTE TRANSPORTING MEMBRANES FOR USE WITH ANALYTE SENSORS", which application is incorporated by reference herein.

BACKGROUND OF THE INVENTION

1. Field of the Invention

Analyte sensors (e.g. glucose sensors used in the management of diabetes) and methods and materials for making and using such sensors.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

One common problem with electrochemical sensors is that they can electrochemically react not only with the analyte to be measured (or by-product of the enzymatic reaction with the analyte), but can also generate signals from other electroactive chemical species present in the analyte environment that are not intentionally being measured, which causes an increase in signal strength due to these "interfering species". Typically, such interfering species are compounds with an oxidation or reduction potential that overlaps with the analyte to be measured (or by-product of the enzymatic reaction with the analyte). For example, in a conventional amperometric glucose oxidase-based glucose sensor wherein the sensor measures hydrogen peroxide, interfering species such as acetaminophen, ascorbate, m-cresol, phenol, glycerol and urate are known to confound true analyte signals.

For the above-noted reasons, methods and materials designed to improve sensor function and address the difficulties caused by such interfering species are desirable. In addition, methods and materials designed to optimize analyte migration through sensor elements are desirable.

SUMMARY OF THE INVENTION

As disclosed herein, problems with spurious electronic signals that can occur in electrochemical analyte sensors as a result of interfering species present in in vivo environments can be overcome by using electrochemical analyte sensors having a constellation of materials selected to allow them to facilitate analyte migration through the sensor and sense true analyte signals while avoiding confounding signals that can be caused by interfering species. In this context, the present invention provides methods and materials designed to improve analyte migration and sensor sensitivity and address the difficulties caused by interfering species present in in vivo environments.

Embodiments of the invention include analyte sensors having an outer membrane comprising a phospholipid bilayer and chemically selective transporter molecules selected to function as a filter and controller of the flux of analyte molecules of interest. In illustrative embodiments of the invention, the membrane of the sensor is formed to have a high selectivity towards glucose, while providing efficient barrier against interfering molecules such as ascorbic acid, acetaminophen, uric acid and the like. Embodiments of the invention also include methods of making such sensors. Embodiments of the invention further include methods of sensing analytes using the analyte sensors disclosed herein.

In certain embodiments of the invention the analyte sensor apparatus comprises a base layer, a conductive layer disposed on the base layer, wherein the conductive layer includes a working electrode; an analyte sensing layer disposed on the working electrode, wherein the analyte sensing layer comprises an enzyme selected to react with an analyte (e.g., glucose oxidase); and an analyte transporting layer disposed over the analyte sensing layer. In such embodiments of the invention, the analyte transporting layer comprises materials that form a phospholipid bilayer; the analyte transporting layer comprises at least one protein selected facilitate transport of the analyte (e.g., GLUT-1) from an environment in which the sensor is disposed to the enzyme; and the analyte transporting layer inhibits the diffusion of at least one of acetaminophen, ascorbate, m-cresol, phenol, glycerol and urate therethrough. In typical embodiments of the invention the enzyme in such analyte sensors comprises a glucose oxidase, a glucose dehydrogenase, a 3-hydroxybutyrate dehydrogenase, or a lactate oxidase. In certain embodiments of the invention, the analyte sensor is designed to sense glucose and the protein disposed in the analyte transporting layer is a glucose transporting protein (e.g., GLUT-1).

Another embodiment of the invention is a method of making an analyte sensor apparatus comprising the steps of providing a base layer; forming a conductive layer on the base layer, wherein the conductive layer includes a working electrode; and then forming an analyte sensing layer over the working electrode, wherein the analyte sensing layer comprises an enzyme selected to react with an analyte. In these methods, an analyte transporting layer is then formed over the analyte sensing layer. Typically in these methods, the analyte transporting layer comprises phospholipids; the analyte transporting layer comprises at least one protein selected facilitate transport of the analyte from an environment in which the sensor is disposed to the enzyme; and the analyte transporting layer is formed from materials selected to inhibit the diffusion of at least one of acetaminophen, ascorbate, m-cresol, phenol, glycerol and urate therethrough. Typically in these methods, the enzyme comprises a glucose dehydrogenase, a 3-hydroxybutyrate dehydrogenase, a lactate oxidase or a glucose oxidase. In certain embodiments of these methods, the analyte sensor is designed to sense glucose and the protein is a glucose transporting protein (e.g. GLUT-1).

In certain embodiments of the methods for making the analyte sensors disclosed herein, the method includes the steps of disposing the analyte transporting layer comprising phospholipids in the sensor, and subsequently incorporating the at least one protein selected facilitate transport of the analyte into a phospholipid bilayer formed by the phospholipids. In other embodiments of these methods, the method includes the steps of combining phospholipids and the at least one protein selected facilitate transport of the analyte; and then disposing this combination in the sensor. In certain embodiments of these methods, amounts of and/or the surface density of phospholipids and/or transporter molecules (e.g. proteins such as GLUT-1) is selected to limit the amount of analyte contacting the enzyme. In some embodiments of these methods, the electrode is formed from platinum using a sputtering process. In certain embodiments of these methods, the at least one protein is chemically synthesized and/or selected to exhibit optimized stability during storage. In some embodiments of these methods, amounts of phospholipids are selected to form an analyte sensor having a user wear time exceeding 14 days.

Yet another embodiment of the invention includes methods of estimating the concentrations of an analyte in vivo, the methods comprising disposing an amperometric analyte sensor disclosed herein into an in vivo environment of a subject, wherein the environment comprises the analyte; and then estimating the concentration of the analyte; so that the concentrations of the analyte in vivo are estimated.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

As shown in FIG. 4, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

DETAILED DESCRIPTION OF THE INVENTION

Figure 1:
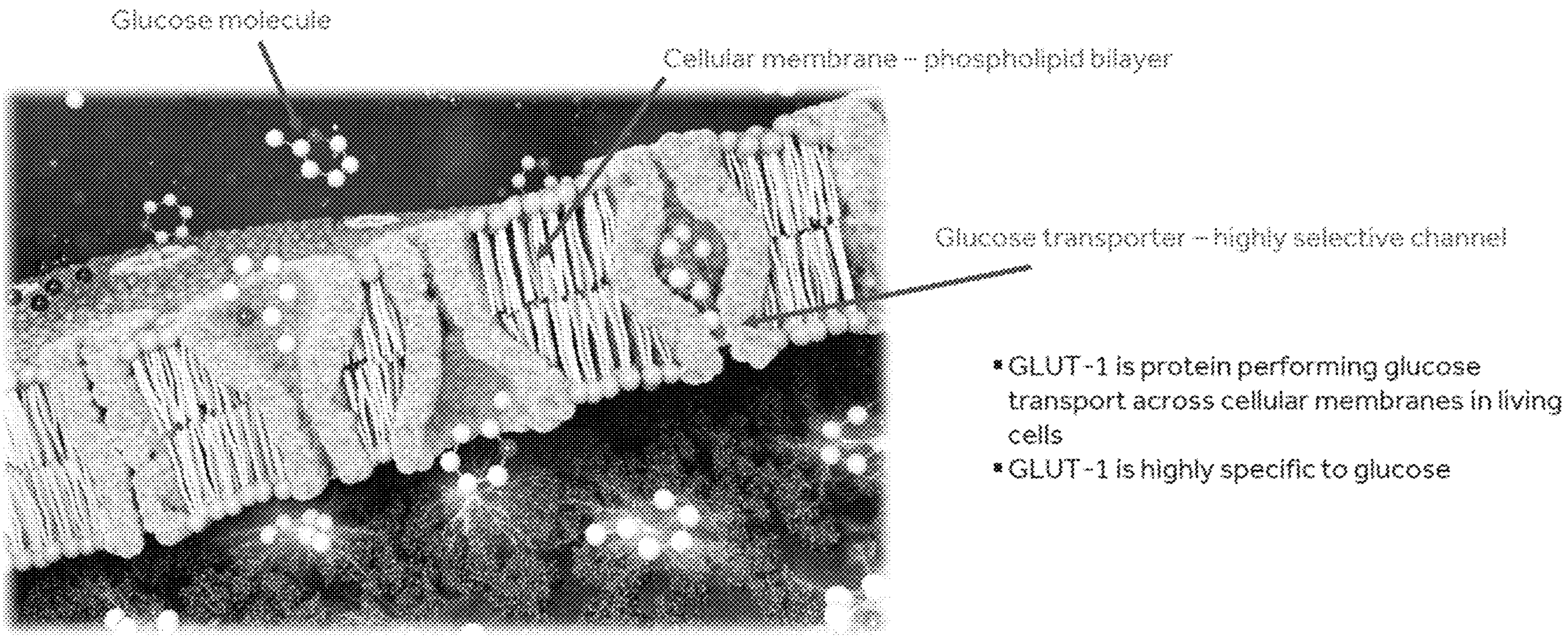
FIG. 1 PRIOR ART
FIG. 1 provides a schematic of an illustrative analyte modulating layer that can be adapted for use with sensors disclosed herein. Such layers made from materials designed to mimic the phospholipid bilayers of cell membranes and include the glucose transporter protein GLUT-1. See Kim et al., Analyst, 2020, 145, 2125.
Figure 2A:
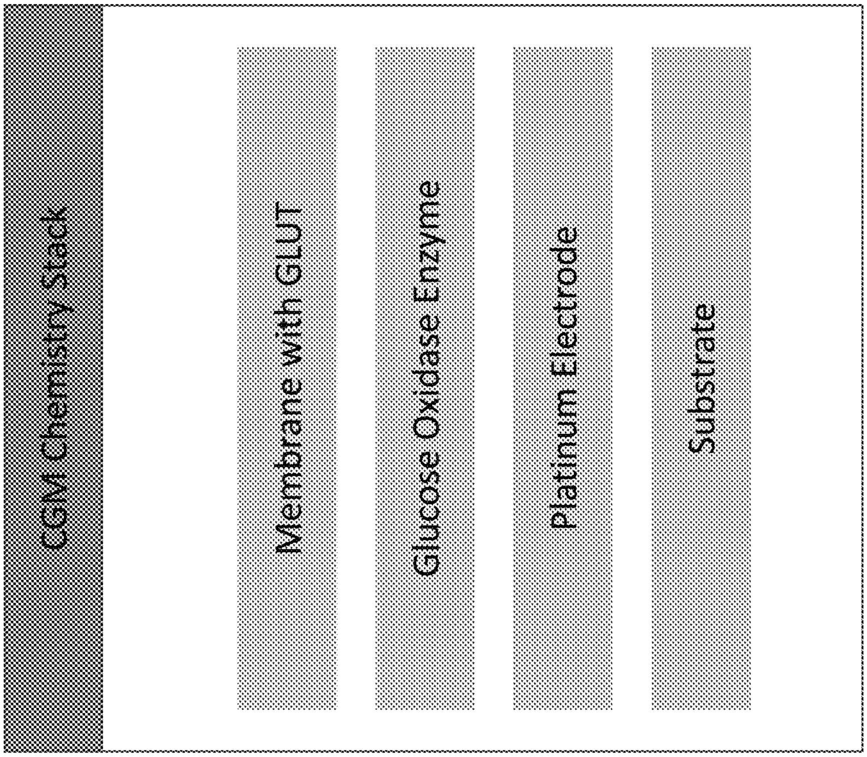
FIGS. 2A-2E provide diagrams of the ways in which various layers can be stacked in glucose oxidase (Gox) based glucose sensors of the invention.
Figure 2B:
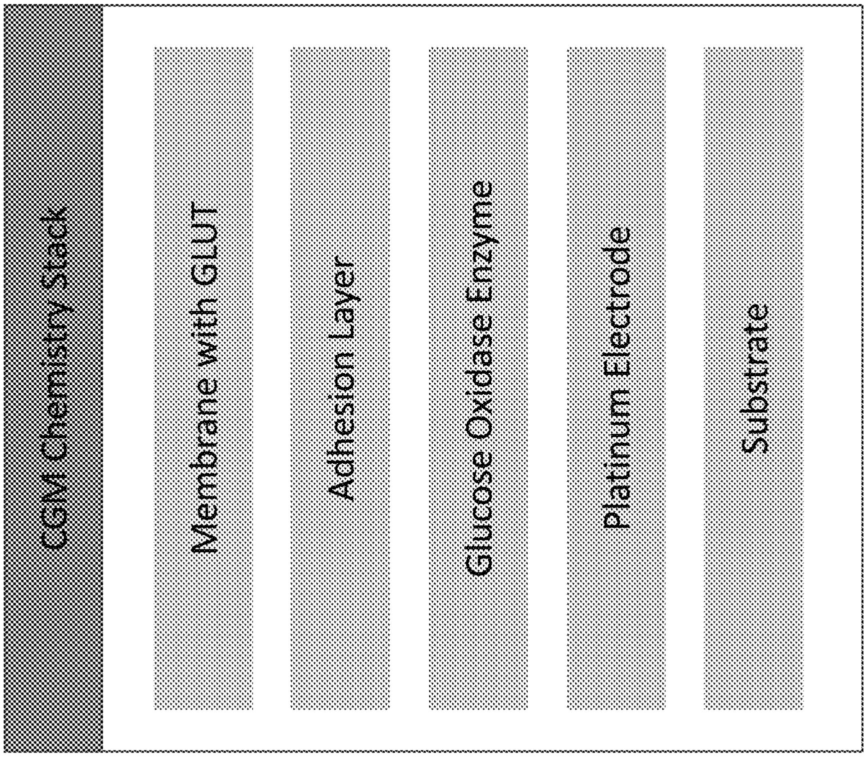
Figure 2C:
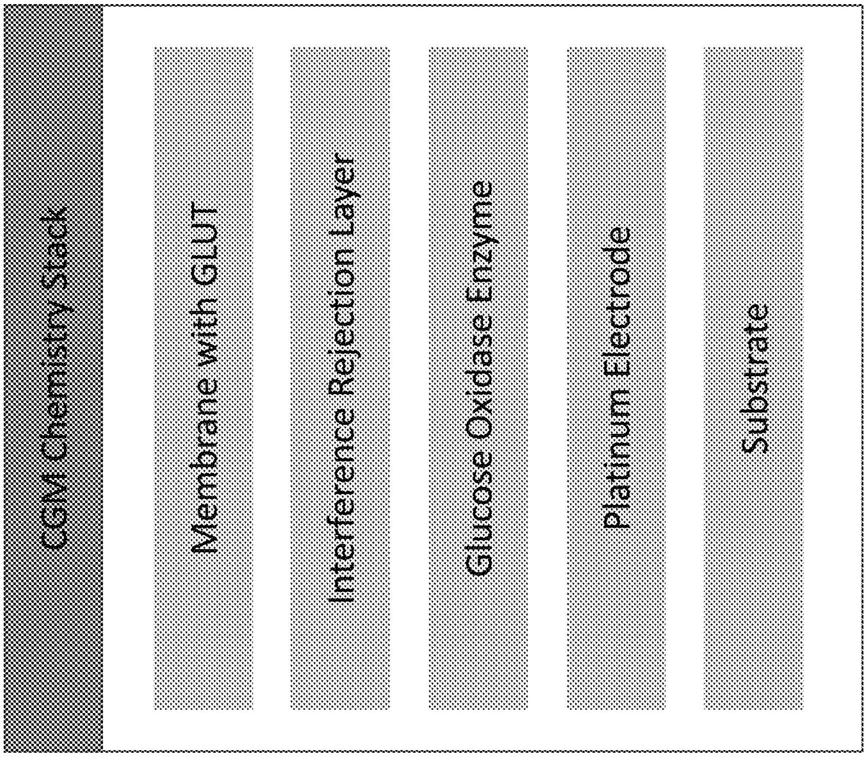
Figure 2D:
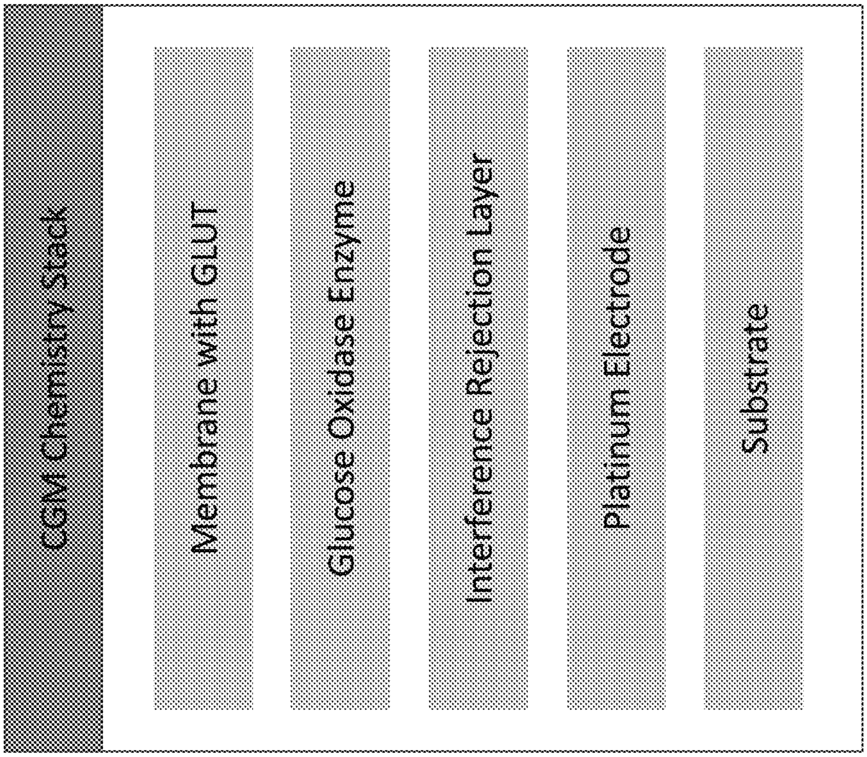
Figure 2E:
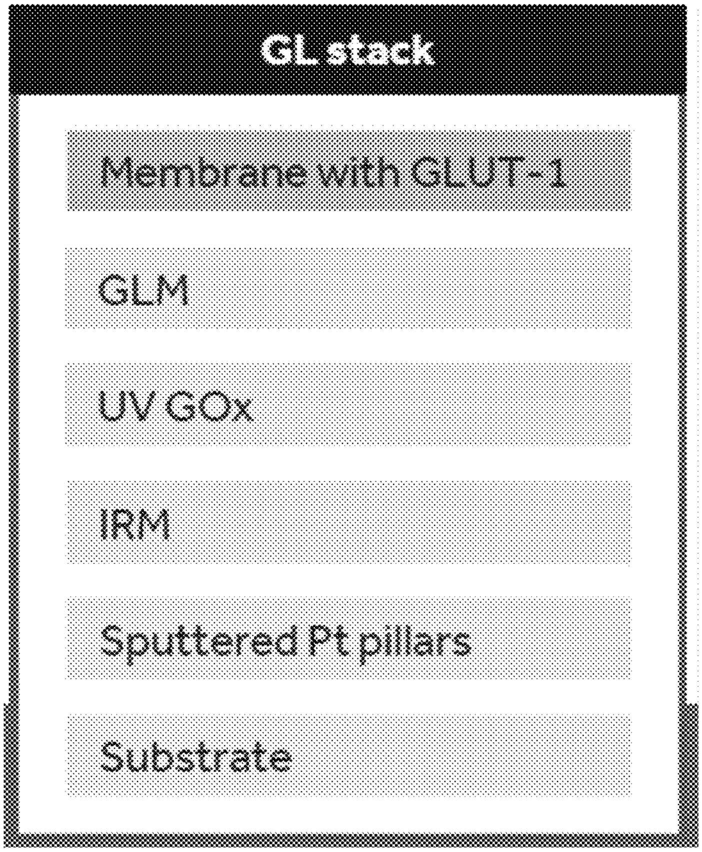

Unless otherwise defined, all terms of art, notations, and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. In addition, certain text from related art is reproduced herein to more clearly delineate the various embodiments of the invention. A number of terms are defined below.

All publications mentioned herein are expressly incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The terms "interferents" and "interfering species/compounds" are used in their ordinary sense, including, but not limited to, effects and/or chemical species/compounds that interfere with the measurement of an analyte of interest in a sensor to produce a signal that does not accurately represent the analyte measurement. In one example of an electrochemical sensor, interfering species are compounds with an oxidation potential that overlaps with the analyte to be measured so as to produce spurious signals.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

With electrochemical glucose sensors that utilize the chemical reaction between glucose and glucose oxidase to generate a measurable signal, various embodiments of the invention are designed to address what is known in the art as the "oxygen deficit problem". Specifically, because glucose oxidase-based sensors require both oxygen ($O_2$) as well as glucose to generate a signal, the presence of an excess of oxygen relative to glucose, is necessary for the operation of a glucose oxidase-based glucose sensor. However, because the concentration of oxygen in subcutaneous tissue is much less than that of glucose, oxygen can be the limiting reactant in the reaction between glucose, oxygen, and glucose oxidase in a sensor—a situation which compromises the sensor's ability to produce a signal that is strictly dependent on the concentration of glucose. In addition, with such electrochemical glucose sensors certain compounds present in fluids in which analytes are sensed (e.g., acetaminophen, cresols and the like) can create spurious, analyte like signals that can interfere with the true measurement of an analyte of interest (i.e., by producing sensor signals that do not represent true analyte).

Living cells have a highly efficient mechanism to deliver glucose across cellular membranes. A family of specialized proteins, glucose transporters, exists in nature to provide a function of highly specific delivery of glucose. In this context, embodiments of the invention incorporate a layer of materials designed to mimic a cell membrane into implantable analyte sensors (e.g. as a layer within a stack of materials used in amperometric glucose sensors). Such layers are formed from a phospholipid bilayer combined with one or more analyte transporters (e.g., GLUT-1). The lipid layer is an efficient barrier against most molecules (this is its key function of such materials in the cells). The presence of analyte/glucose transporters in such layers then provides high analyte selectivity, thereby achieving interferant rejection function. The amounts of analyte transporters used in such materials are selected to regulate the amount of analyte/glucose being transported, thereby achieving analyte/glucose modulating functions. Additionally, another benefit of sensors comprising outer layers of such materials is increased biocompatibility and wear time of the sensor, given that the outer layer mimics cellular membranes.

As discussed in detail below, embodiments of the invention relate to the use of an electrochemical sensor that includes an analyte transporting layer made from materials that allows this layer to act both as an analyte transporting membrane as well as an interferent rejecting membrane. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise one or more membranes surrounding the enzyme through which an analyte migrates. The product is then measured using electrochemical methods and thus the output of an electrode system functions as a measure of the analyte.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. an analyte transporting membrane comprising a phospholipid bilayer and a glucose transporting protein) can be adapted for use with any one of the wide variety of sensors known in the art. The analyte sensor elements, architectures, and methods for making and using these elements that are disclosed herein can be used to establish a variety of layered sensor structures.

Specific aspects of embodiments of the invention are discussed in the following sections.

Typical Elements, Configurations and Analyte Sensor Embodiments of the Invention A wide variety of sensors and sensor elements are known in the art including amperometric sensors used to detect and/or measure biological analytes such as glucose. Many glucose sensors are based on an oxygen (Clark-type) amperometric transducer (see, e.g. Yang et al., Electroanalysis 1997, 9, No. 16:1252-1256; Clark et al., Ann. N.Y. Acad. Sci. 1962, 102, 29; Updike et al., Nature 1967, 214,986; and Wilkins et al., Med. Engin. Physics, 1996, 18, 273.3-51). A number of in vivo glucose sensors utilize hydrogen peroxide-based amperometric transducers because such transducers are relatively easy to fabricate and can readily be miniaturized using conventional technology. A problem associated with the use of hydrogen peroxide-based amperometric transducers, however, is signal interference due to electroactive substances present in the analyte environment. Current sensors in the art commonly lack selectivity against other electrochemically reactive substances such as acetaminophen and other drugs, which would lead to significant false signals if not eliminated.

A variety of electrochemical analyte sensors function by applying an electrical potential to one or more sensor electrodes that are designed to provide different electronic signals in the presence of an analyte of interest (e.g., electrochemical glucose sensors that are used by diabetic individuals). In such electrochemical analyte sensors, problems can arise when an electrical operating potential applied to the electrode generates signals that are not only associated with the presence of analyte, but also generate signals in response to the presence of non-analyte agents present in the environment in which the analyte is sensed. For example, in electrochemical glucose sensors that are designed to apply relatively high electrode potentials to the sensor electrode(s)

(e.g., an applied potential of 535 mV) spurious non-analyte signals are observed for interferents such as certain drugs a patient may be taking (e.g., acetaminophen), and/or additives commonly combined with insulin formulation that are administered to diabetic patients (e.g., m-cresol, phenol and glycerol).

Embodiments of the invention include, for example, methods of making an analyte sensor apparatus, including ones having a membrane that serves dual purposes of: (1) facilitating the transport of an analyte therethrough in order to, for example, avoid the oxygen deficit problem in glucose oxidase based sensors; and (2) inhibiting the diffusion of interferents from an in vivo environment to sensor electrodes. In this way, a single layer/membrane acts as both an analyte transporting layer and an interference rejection layer in the sensors disclosed herein. Methods of the invention include forming an analyte sensor apparatus via the steps of providing a base layer; forming a conductive layer on the base layer, wherein the conductive layer includes a working electrode; and then forming an analyte sensing layer over the working electrode, wherein the analyte sensing layer comprises an enzyme selected to react with an analyte. In these methods, an analyte transporting layer is then formed over the analyte sensing layer. Typically in these methods, the analyte transporting layer comprises phospholipids (e.g. in the form of natural or synthetic phospholipid membranes); and at least one transport protein selected facilitate transport of the analyte from an environment in which the sensor is disposed to the enzyme (e.g. in the form of natural or synthetic transport polypeptides). In this way, the analyte transporting layer is formed from materials selected to inhibit the diffusion of at least one of acetaminophen, ascorbate, m-cresol, phenol, glycerol and urate therethrough. In such embodiments of the invention, the phospholipid layer blocks interferants from accessing sensor elements while the transporter protein (e.g. GLUT-1) functions to transport a selected analyte into the sensor and in this way further provide selectivity/interference rejection. In certain embodiments of the invention, the amounts or density of a transporter protein is adjusted to control analyte/glucose flux.

Typically in these methods, the enzyme comprises a glucose dehydrogenase, a 3-hydroxybutyrate dehydrogenase, a lactate oxidase or a glucose oxidase. In certain embodiments of these methods, the analyte sensor is designed to sense glucose and the protein is a glucose transporting protein. In this context, glucose transport can be effected by two families of glucose transporters: the GLUT family and SGLT family. The GLUT family consists of 14 different types of glucose transporters from GLUT-1, GLUT-2, and GLUT-3 to GLUT-14. The SGLT family consists of sodium-glucose cotransporters, including SGLT1 and SGLT2.

In certain embodiments of the methods for making the analyte sensors disclosed herein, the method includes the steps of disposing the analyte transporting layer comprising phospholipids in the sensor, and subsequently incorporating the at least one protein selected facilitate transport of the analyte into a phospholipid bilayer formed by the phospholipids. In other embodiments of these methods, the method includes the steps of combining phospholipids and the at least one protein selected facilitate transport of the analyte; and then disposing this combination in the sensor. In certain embodiments of these methods, amounts of and/or the surface density of transporter molecules (e.g. proteins such as GLUT-1) is selected to limit the amount of analyte contacting the enzyme. In some embodiments of these methods, the electrode is formed from platinum using a sputtering process. In certain embodiments of these methods, the at least one protein is chemically synthesized and/or selected to exhibit optimized stability during storage. In some embodiments of these methods, amounts of phospholipids are selected to form an analyte sensor having a user wear time exceeding 14 days.

Embodiments of the invention can be made according to art accepted practices. For example, a sensor membrane that combines interference rejection and analyte/glucose limiting functionalities by making a composition comprising phospholipid bilayers via an art accepted methods and materials such as those disclosed in U.S. Patent Application Publication No. 20220153778; Huang et al, J. R. Soc. Interface 2021 February; 18 (175) 20200860: (microfluidics/Oil in water/Droplet transfer); Tang et al., NATURE PROTOCOLS, VOL. 12 NO. 12 (2017) 2554-2569; Zuo et al., J. Pept. Sci. 2015; 21:540-549; Podolsky et al., Nature Reviews Chemistry volume 5, pages 676-694 (2021); Zheng et al., J. Am. Chem. Soc. 2016, 138, 10, 3553-3561; Zhao et al.; Analytica Chimica Acta 1226 (2022) 340263; Hansen et al., Chem Commun (Camb). 2015 Feb. 11; 51 (12): 2316-9; and Kim et al., Analyst, 2020, 145, 2125 (generating lipid layers from RBCs), the contents of which are incorporated by reference. In addition, certain commercially available materials can be adapted for use in embodiments of the invention (see, https://www.creative-biostructure.com/MemPro%E2%84%A2-Glucose-transporter-106.htm and https://www.mybiosource.com/recombinant-protein/glucose-transporter-2-glut2/2097532). Membranes made by such methods can be stored in CHCl3. Certain embodiments of the invention further combine such membrane compositions with a glucose transporter polypeptide such as GLUT-1. This can include suspending GLUT-1 in ultra-pure Sucrose buffer (e.g., range: 10 mM-40 mM range change as necessary to maintain osmolarity). In this context, glucose transporter polypeptides such as GLUT-1 are well known in the art. See, e.g., Boado et al., Molecular and Cellular Neuroscience Volume 1, Issue 3, December 1990, Pages 224-232.

Methods of the invention can include combining a glucose transporter polypeptide with stabilizing agents such as LMP-Agarose (e.g., 0.2-1% range offers stability particularly at extreme temperatures) or very low concentrated gelatin (e.g., 0.2-1% range) to form large vesicles. Methods of the invention include forming and coating at the bilayer/transporter combination material with a mixture of polar lipids and of Cholesterol. Certain embodiments of the invention typically aim for at least 25-30% range. A CH3OH—CHCl3 mixture-Offers fluidity/elasticity to the membrane. One can then characterize Membrane-Active polypeptides in Oriented Lipid Bilayers using a Circular Dichroism protocol such as the one disclosed in Bürck et al., Acc Chem Res. 2016 Feb. 16; 49(2):184-92. Method steps of the invention can include allowing the coated mixture to dry. Dried materials can be reconstituted in a buffered aqueous solution that approximates physiological conditions such as Hank's balanced salt solution (HBSS) and further agents (e.g., 2-5 mM Glucose and 0.5 mM KCl range).

Embodiments of the invention can utilize methods and materials from related technologies such as those disclosed in Neumann-Spallart et al., Applied Biochemistry and Biotechnology volume 68, pages 153-169 (1997). Transporter proteins such as GLUT-1 are commercially available (see, e.g. https://www.abcam.com/human-glucose-transporter-glut1-peptideab33006; and https://www.abcam.com/glucose-transporter-glut1-peptideab202335.html). Analyte sensing enzymes such as glucose oxidase (GOx) can be immobilized in the sensor using avidin immobilization and/or glutaraldehyde, optionally followed by Electropolymerization of o-phenylene diamine. Embodiments of the invention can include the steps of biotinylating GLUT-1 containing vesicles. Such embodiments of the invention can include the step of reconstituting GLUT-1 vesicles and then coating them on an avidinated GOX layer as noted above.

Embodiments of the invention include the steps of utilizing a chemically synthesized transporter protein such as GLUT-1, or alternatively utilizing a transporter protein derived from a biological sources such as cell culture. Embodiments of the invention include the steps of generating artificial bilayers (e.g. via microfluidics/oil in water/droplet transfer)/or generate lipid layers from RBCs. Such bilayers can be stored in CHCl3. In certain embodiments of the invention, artisans can assemble GLUT-1+Bilayers using circular dichroism to confirm the transporter membrane insertion into the bilayer). Certain methods of the invention include the step of suspending a transporter protein such as GLUT1 in ultrapure sucrose buffer (at around 40 mM, with changes to concentration as necessary to maintain osmolarity). Methods of the invention include the step of mixing transporter proteins with stabilizing agents such as LMP-Agarose (offers stability particularly at extreme temperatures) or very low concentrations of gelatin to form large vesicles. In can let these compositions dry. Methods of the invention include the step of coating such vesicles with mixture of polar lipids and of cholesterol (e.g., at least 25-30% CH3OH—CHCl3 mixture). Methods of the invention include the step of drying such coated vesicles. Methods of the invention include the step of reconstituting dried coated vesicles with HBSS and (e.g. in 5 mM Glucose and 0.5 mM KCl).

Embodiments of the invention include analyte sensors having an outer membrane comprising a phospholipid bilayer and chemically selective transporter molecules selected to function as a filter and controller of the flux of analyte molecules of interest. In illustrative embodiments of the invention, the membrane of the sensor is formed to have a high selectivity towards glucose, while providing efficient barrier against interfering molecules such as ascorbic acid, acetaminophen, uric acid and the like. Embodiments of the invention also include methods of making such sensors. Embodiments of the invention further include methods of sensing analytes using the analyte sensors disclosed herein.

In certain embodiments of the invention the analyte sensor apparatus comprises a base layer, a conductive layer disposed on the base layer, wherein the conductive layer includes a working electrode; an analyte sensing layer disposed on the working electrode, wherein the analyte sensing layer comprises an enzyme selected to react with an analyte; and an analyte transporting layer disposed over the analyte sensing layer. In such embodiments of the invention, the analyte transporting layer comprises materials that form a phospholipid bilayer; the analyte transporting layer comprises at least one protein selected facilitate transport of the analyte from an environment in which the sensor is disposed to the enzyme; and the analyte transporting layer inhibits the diffusion of at least one of acetaminophen, ascorbate, m-cresol, phenol, glycerol and urate therethrough. In typical embodiments of the invention the enzyme in such analyte sensors comprises a glucose oxidase, a glucose dehydrogenase, a 3-hydroxybutyrate dehydrogenase, or a lactate oxidase. In certain embodiments of the invention, the analyte sensor is designed to sense glucose and the protein disposed in the analyte transporting layer is a glucose transporting protein (e.g., GLUT-1).

Embodiments of the invention also include methods of estimating the concentrations of an analyte (e.g. glucose, lactate, 3-hydroxybutyrate or the like) in vivo. Typically, such methods include disposing an amperometric analyte sensor disclosed herein into an in vivo environment of a subject, wherein the environment comprises the analyte; and then estimating the concentration of the analyte; so that the concentrations of the analyte in vivo are estimated.

In some embodiments of the invention, the conductive layer comprises a plurality of electrodes including the working electrode, a counter electrode and a reference electrode. Optionally, the conductive layer comprises a plurality of working electrodes, counter electrodes and reference electrodes; and the plurality of working, counter, and reference electrodes are grouped together as a unit and positionally distributed on the conductive layer in a repeating pattern of units. In some embodiments of the invention, the sensor is operatively coupled to: a sensor input capable of receiving a signal from the sensor that is based on a sensed physiological characteristic value in the mammal; and a processor coupled to the sensor input, wherein the processor is capable of characterizing one or more signals received from the sensor. In certain embodiments of the invention, a pulsed voltage is used to obtain a signal from an electrode.

Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described herein.

Analyte Transporting and Interference Rejection Constituent

Embodiments of the invention include analyte sensors having an outer analyte transporting layer comprising a phospholipid bilayer and chemically selective transporter molecules (e.g. GLUT-1) selected to function as a filter and controller of the flux of analyte molecules of interest. In illustrative embodiments of the invention, the membrane of the sensor is formed to have a high selectivity towards glucose, while providing efficient barrier against interfering molecules such as ascorbic acid, acetaminophen, uric acid and the like. Embodiments of the invention include the steps of selecting a transporter protein such as GLUT-1 for use in the sensor and include the steps of generating artificial phospholipid bilayers (e.g. via microfluidics/oil in water/droplet transfer)/or generate lipid layers from RBCs in which the transporting protein is disposed. In certain embodiments of the invention, artisans can assemble transporting protein combined with lipid bilayers using circular dichroism to confirm the transporter protein insertion into the bilayer.

Base Constituent

Sensors of the invention typically include a base constituent. The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment the base constituent comprises a ceramic. Alternatively, the base constituent comprises a polymeric material such as a polyimmide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for measuring an analyte or its byproduct (e.g. oxygen and/or hydrogen peroxide) to be assayed. The term “conductive constituent” is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent. Examples of useful materials for generating this protective cover constituent include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a “nanostructured material” is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention can include a separate interference rejection constituent disposed between the surface of the electrode and the environment to be assayed, for example one specific to acetaminophen. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids, such as acetaminophen. In this context, the term “interference rejection constituent” is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size).

Analyte Sensing Constituent

The electrochemical sensors of the invention include an analyte sensing constituent disposed on the electrodes of the sensor. The term “analyte sensing constituent” is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with, for example, the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture.

Protein Constituent

The electrochemical sensors of the invention optionally include a protein constituent disposed between the analyte sensing constituent and the analyte modulating constituent. The term "protein constituent" is used herein according to art accepted terminology and refers to a constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents. The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase ($GO_x$) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such as the analyte sensing constituent and/or the protein constituent and/or a siloxane moiety present in a compound disposed in a proximal layer such as the analyte modulating layer.

High-Density Amine Constituent

The electrochemical sensors of the invention can include one or more high-density amine constituent layers that provide the sensors with a number of beneficial functions. Such layers can optimize sensor function, for example by acting as an adhesion promoting constituent for layers adjacent to the HDA layer, by decreasing fluctuations that can occur in glucose sensors by improving sensor initialization profiles and the like. Typically, the high-density amine constituent is disposed between and in direct contact with the analyte sensing constituent and the analyte modulating constituent. In typical embodiments, the high-density amine layer comprises poly-l-lysine having molecular weights between 30 KDa and 300 KDa (e.g. between 150 KDa and 300 KDa). The concentrations of poly-l-lysine in such high-density amine layers is typically from 0.1 weight-to-weight percent to 0.5 weight-to-weight percent and the high-density amine layer 500 is from 0.1 to 0.4 microns thick.

Analyte Modulating Constituent

The electrochemical sensors of the invention include an analyte modulating constituent disposed on the sensor. The term "analyte modulating constituent" (e.g. a glucose limiting membrane or "GLM") is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane (e.g. a glucose limiting membrane) which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g., glucose), while at the same time allowing or even facilitating the diffusion of other types of molecules through the constituent (e.g. $O_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

Cover Constituent

The electrochemical sensors of the invention include one or more cover constituents which are typically electrically insulating protective constituents. Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Typical Analyte Sensor System Embodiments of the Invention

Embodiments of the sensor elements and sensors disclosed herein can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

Illustrative Analyte Sensor Systems of the Invention

A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

Figure 3:
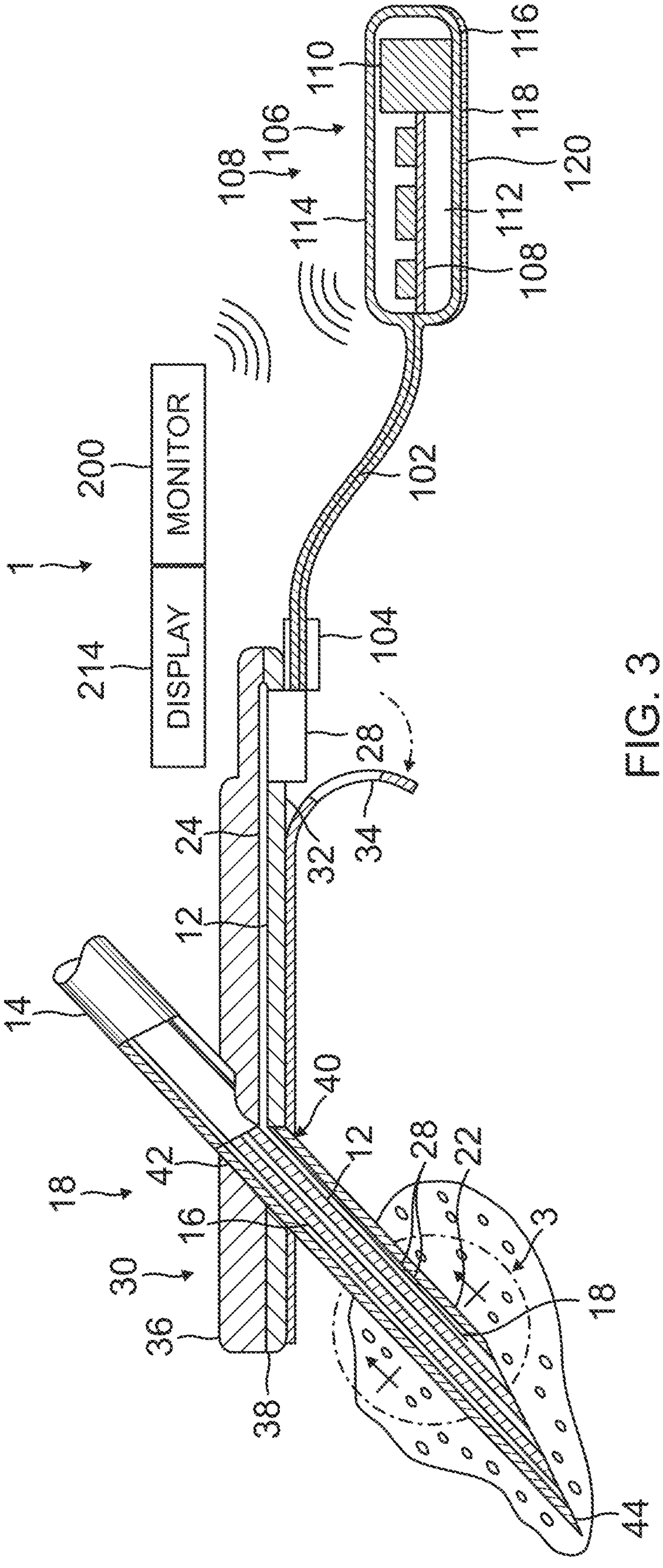
FIG. 3 provides a perspective view illustrating a subcutaneous sensor insertion set, a telemetered characteristic monitor transmitter device, and a data receiving device embodying features of the invention.
Figure 4:
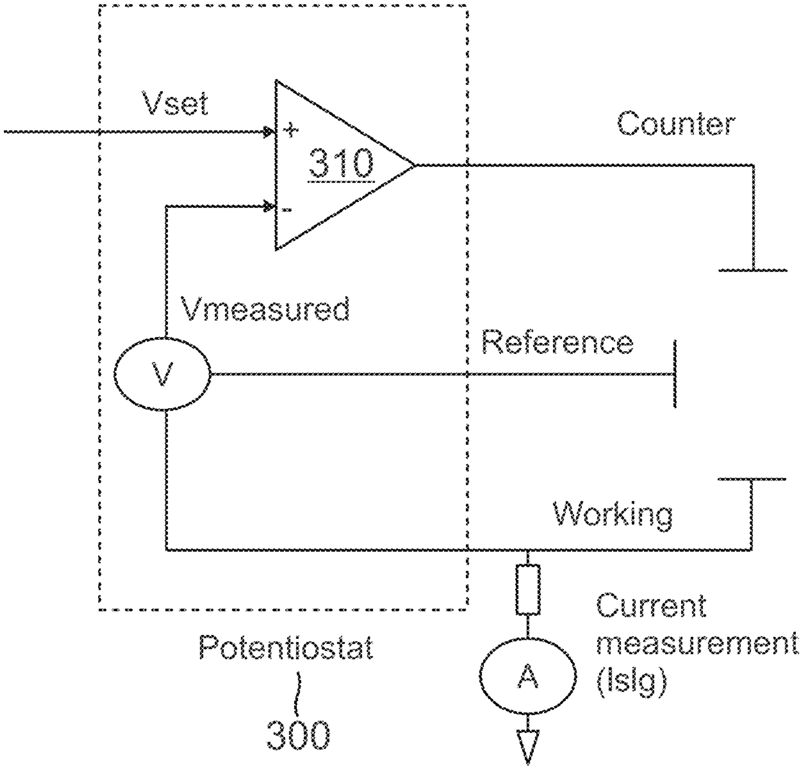
FIG. 4 shows a schematic of a potentiostat that may be used to measure current in embodiments of the present invention.

FIG. 3 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 3 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 100 by a connector block 28 (or the like).

As shown in FIG. 3, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 100 is coupled to a sensor set 10 by a cable 102 through a connector 104 that is electrically coupled to the connector block 28 of the connector portion 24 of the sensor set 10.

In the embodiment shown in FIG. 3, the telemetered characteristic monitor 100 includes a housing 106 that supports a printed circuit board 108, batteries 110, antenna 112, and the cable 102 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated, and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 100 is ready for use.

In the illustrative embodiment shown in FIG. 3, the subcutaneous sensor set 10 facilitates accurate placement of a flexible thin film electrochemical sensor 12 of the type used for monitoring specific blood parameters representative of a user's condition. The sensor 12 monitors glucose levels in the body and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

In the illustrative embodiment shown in FIG. 3, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream or may be placed in a subcutaneous or peritoneal region of the human body.

In the embodiment of the invention shown in FIG. 3, the monitor of sensor signals 200 may also be referred to as a sensor electronics device 200. The monitor 200 may include a power source, a sensor interface, processing electronics (i.e., a processor), and data formatting electronics. The monitor 200 may be coupled to the sensor set 10 by a cable 102 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

General Methods for Making Analyte Sensors

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming a forming an analyte sensing layer over the conductive layer, wherein the analyte sensing layer includes constituents that can alter the electrical current at the electrode in the conductive layer in the presence of an analyte; forming an analyte transporting layer, wherein the analyte transporting layer includes a composition that modulates the diffusion of the analyte therethrough while inhibiting the diffusion of interferents therethrough.

As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose dehydrogenase, 3-hydroxybutyrate dehydrogenase, lactate oxidase, glucose oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a analyte sensing enzyme layer can then be disposed on the sensing layer by electrochemical deposition or a method other than electrochemical deposition such a spin coating, followed by vapor crosslinking, for example with a dialdehyde (glutaraldehyde) or a carbodiimide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, New York (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

In an illustrative sensor embodiment for use as a glucose sensor, an enzyme (typically glucose oxidase) is coated with the enzyme so as to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor. Methods for producing the enzyme coatings include spin coating processes, dip and dry processes, low shear spraying processes, ink-jet printing processes, silk screen processes and the like. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

The invention claimed is:

1. An analyte sensor apparatus comprising:

a base layer;

a conductive layer disposed on the base layer, wherein the conductive layer includes a working electrode comprising platinum;

an analyte sensing layer disposed on the working electrode, wherein the analyte sensing layer comprises an enzyme selected to react with an analyte; and an analyte transporting layer disposed over the analyte sensing layer, wherein:

the analyte transporting layer comprises materials that form a synthetic phospholipid bilayer; and the analyte transporting layer comprises at least one protein selected to facilitate transport of the analyte from an environment in which the sensor is disposed to the enzyme; and the analyte transporting layer inhibits the diffusion of at least one of acetaminophen, ascorbate, m-cresol, phenol, glycerol and urate therethrough.

2. The analyte sensor apparatus of claim 1, wherein: the enzyme comprises a glucose oxidase, a glucose dehydrogenase, a 3-hydroxybutyrate dehydrogenase, or a lactate oxidase; and/or the analyte sensor apparatus further comprises an analyte modulating membrane.

3. The analyte sensor apparatus of claim 1, wherein the protein disposed in the analyte transporting layer is a glucose transporting protein.

4. The analyte sensor apparatus of claim 3, wherein the protein is GLUT-1.

5. A method of estimating the concentrations of an analyte in vivo, the method comprising:

disposing an amperometric analyte sensor of claim 1 into an in vivo environment of a subject, wherein the environment comprises the analyte; and estimating the concentration of the analyte;

so that the concentrations of the analyte in vivo are estimated.

6. A method of making an analyte sensor apparatus comprising the steps of:

providing a base layer;

forming a conductive layer on the base layer, wherein the conductive layer includes a working electrode comprising platinum;

forming an analyte sensing layer over the working electrode, wherein the analyte sensing layer comprises an enzyme selected to react with an analyte; and forming an analyte transporting layer over the analyte sensing layer, wherein:

the analyte transporting layer comprises a synthetic phospholipid composition;

the analyte transporting layer comprises at least one protein selected to facilitate transport of the analyte from an environment in which the sensor is disposed to the enzyme; and the analyte transporting layer is formed from materials selected to inhibit the diffusion of at least one of acetaminophen, ascorbate, m-cresol, phenol, glycerol and urate therethrough.

7. The method of claim 6, wherein: the enzyme comprises a glucose dehydrogenase, a 3-hydroxybutyrate dehydrogenase, a lactate oxidase or a glucose oxidase.

8. The method of claim 7, wherein the protein is a glucose transporting protein.

9. The method of claim 8, wherein the protein is GLUT-1.

10. The method of claim 6, wherein the method includes the steps of disposing the analyte transporting layer comprising the synthetic phospholipid composition in the sensor, and subsequently incorporating the at least one protein selected to facilitate transport of the analyte into a phospholipid bilayer formed by the synthetic phospholipid composition.

11. The method of claim 6, wherein the method includes the steps of combining the synthetic phospholipid composition and the at least one protein selected to facilitate transport of the analyte; and then disposing this combination in the analyte sensor apparatus.

12. The method of claim 6, wherein amounts of and/or the surface density of transporter molecules is selected to limit the amount of analyte contacting the enzyme.

13. The method of claim 6, wherein the electrode is formed from platinum using a sputtering process.

14. The method of claim 6, wherein the at least one protein is chemically synthesized and/or selected to exhibit stability during storage.

15. The method of claim 6, wherein amounts of phospholipids in the synthetic phospholipid composition are selected to form an analyte sensor having a user wear time exceeding 14 days.

* * * * *